United States Patent
Ren et al.

(10) Patent No.: US 8,848,982 B2
(45) Date of Patent: Sep. 30, 2014

(54) IMAGE RECONSTRUCTION BY POSITION AND MOTION TRACKING

(71) Applicant: California Institute of Technology, Pasadena, CA (US)

(72) Inventors: Jian Ren, Pasadena, CA (US); Changhuei Yang, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 13/664,032

(22) Filed: Oct. 30, 2012

(65) Prior Publication Data
US 2013/0058533 A1    Mar. 7, 2013

Related U.S. Application Data

(63) Continuation of application No. 12/397,152, filed on Mar. 3, 2009, now Pat. No. 8,325,988.

(60) Provisional application No. 61/068,138, filed on Mar. 3, 2008.

(51) Int. Cl.
| | |
|---|---|
| *G06K 9/00* | (2006.01) |
| *A61B 1/00* | (2006.01) |
| *A61B 5/06* | (2006.01) |
| *G06T 11/00* | (2006.01) |
| *A61B 3/10* | (2006.01) |
| *A61B 1/313* | (2006.01) |
| *A61B 3/00* | (2006.01) |
| *A61B 5/00* | (2006.01) |

(52) U.S. Cl.
CPC .............. *A61B 3/0008* (2013.01); *A61B 5/6848* (2013.01); *A61B 1/00009* (2013.01); *A61B 5/064* (2013.01); *G06T 11/006* (2013.01); *A61B 3/102* (2013.01); *A61B 5/0066* (2013.01); *A61B 5/065* (2013.01); *G06T 2211/436* (2013.01); *A61B 5/0084* (2013.01); *A61B 1/313* (2013.01)
USPC .......................................................... 382/103

(58) Field of Classification Search
USPC .......................... 382/128–134; 128/920–925; 356/39–49; 600/407–414, 424–426; 345/581–618; 250/455
See application file for complete search history.

(56) References Cited

U.S. PATENT DOCUMENTS

| | | | |
|---|---|---|---|
| 2004/0039312 | A1 | 2/2004 | Hilstead et al. |
| 2006/0064016 | A1* | 3/2006 | Demi et al. .................. 600/450 |

(Continued)

OTHER PUBLICATIONS

Herz, P. et al., "Micromotor endoscope catheter for in vivo, ultrahigh-resolution optical coherence tomography," Optics Letters, vol. 29, No. 19, Oct. 1, 2004, pp. 2261-2263.

(Continued)

*Primary Examiner* — Atiba O Fitzpatrick
(74) *Attorney, Agent, or Firm* — Gates & Cooper LLP

(57) ABSTRACT

A system, method, and apparatus provide the ability to reconstruct an image from an object. A hand-held image acquisition device is configured to acquire local image information from a physical object. A tracking system obtains displacement information for the hand-held acquisition device while the device is acquiring the local image information. An image reconstruction system computes the inverse of the displacement information and combines the inverse with the local image information to transform the local image information into a reconstructed local image information. A display device displays the reconstructed local image information.

20 Claims, 7 Drawing Sheets

(56) References Cited

U.S. PATENT DOCUMENTS

| | | | |
|---|---|---|---|
| 2006/0146168 A1 | 7/2006 | Nishi et al. | |
| 2006/0227221 A1* | 10/2006 | Okubo | 348/208.2 |
| 2009/0103791 A1* | 4/2009 | Suri et al. | 382/131 |
| 2010/0280315 A1* | 11/2010 | Pan | 600/109 |

OTHER PUBLICATIONS

Huang, D. et al., "Optical coherence tomography," Science, vol. 254, No. 5035, Nov. 22, 1991, pp. 1178-1181.

Kelling, G., "Endoscopy of the esophagus and stomach," The Lancet, Apr. 28, 1900, pp. 1189-1198.

Killian, G., "On direct endoscopy of the upper air passages and oesophagus," British Medical Journal, Aug. 30, 1902, pp. 569-571.

Li, X. et al., "Imaging needle for optical coherence tomography," Optics Letters, vol. 25, No. 20, Oct. 15, 2000, pp. 1520-1522.

Liu, X. et al., "Rapid-scanning forward-imaging miniature endoscope for real-time optical coherence tomography," Optics Letters, Aug. 1, 2004, vol. 29, No. 15, pp. 1763-1765.

Machemer, R., "The development of pars plana vitrectomy: a personal account," Graefe's Arch. Clin. Exp. Ophthamol., 233, 1995, pp. 453-468.

Povazay, B. et al., "Enhanced visualization of choroidal vessels using ultrahigh resolution ophthalmic OCT at 1050 nm," Optics Express, vol. 11, No. 17, Aug. 25, 2003, pp. 1980-1986.

Schmitt, J. et al., "An optical coherence microscope with enhanced resolving power in thick tissue," Optics Communications, 142, Oct. 15, 1997, pp. 203-207.

Su, J. et al., "In vivo three-dimensional microelectromechanical endoscopic swept source optical coherence tomography," Optics Express, vol. 15, No. 16, Aug. 6, 2007, pp. 10390-10396.

Tearney, G. et al., "Scanning single-mode fiber optic catheter-endoscope for optical coherence tomography," Optics Letters, vol. 21, No. 7, Apr. 1, 1996, pp. 543-545.

Wu, J. et al., "Paired-angle-rotation scanning optical coherence tomography forward-imaging probe," Optics Letters, vol. 31, No. 9, May 1, 2006, pp. 1265-1267.

Xie, T. et al., "Endoscopic optical coherence tomography with a modified microelectromechanical systems mirror for detection of bladder cancers," Applied Optics, vol. 42, No. 31, Nov. 1, 2003, pp. 6422-6426.

Xie, T. et al., "GRIN lens rod based probe for endoscopic spectral domain optical coherence tomography with fast dynamic focus tracking," Optics Express, vol. 14, No. 8, Apr. 17, 2006, pp. 3238-3246.

* cited by examiner

IMAGE RECONSTRUCTION BY POSITION AND MOTION TRACKING

CROSS-REFERENCE TO RELATED APPLICATIONS

This application is a continuation of and claims the benefit under 35 U.S.C. Section 120 of the following commonly-assigned U.S. Utility patent application(s), which is/are incorporated by reference herein:

Utility application Ser. No. 12/397,152, filed on Mar. 3, 2009, by Jian Ren and Changhuei Yang, entitled "Image Reconstruction by Position and Motion Tracking", which application claims the benefit under 35 U.S.C. Section 119(e) of U.S. Provisional Application Ser. No. 61/068,138, filed on Mar. 3, 2008, by Jian Ren and Changhuei Yang, entitled "Image Reconstruction by Position and Movement Tracking in OCT-based hand-held endoscope."

BACKGROUND OF THE INVENTION

1. Field of the Invention

The present invention relates generally to image reconstruction, and in particular, to a method, apparatus, and article of manufacture for eliminating distortion and skew due to the shaking and vibration in hand-held imaging devices such as optical coherence tomography (OCT)-based endoscopes.

2. Description of the Related Art (Note: This application references a number of different publications as indicated throughout the specification by reference numbers enclosed in brackets, e.g., [x]. A list of these different publications ordered according to these reference numbers can be found below in the section entitled "References." Each of these publications is incorporated by reference herein.)

Optical Coherence Tomography (OCT) has been an emerging technology in the field of biomedical imaging since its invention in the 1990s. Its non-invasive nature and high resolution imaging capability makes itself one of the most desirable way imaging biological tissues [1]. Despite its many intriguing advantages, light scattering and/or absorption of tissue are jeopardizing the use of OCT in deep-tissue imaging. For instance, OCT permits only millimeter scale penetration depth for near infrared light [2]. As a potential solution, OCT-based endoscopes, such as an endoscopic needle probe, are capable of penetrating deep into tissues and collecting reflected optical signals from the required depth, which will be further used to reconstruct the structure of the tissue [3-9].

Many OCT-based needle endoscopes have been developed, regardless of their region of inspection, side-imaging [3-6] or forward-imaging [7-10]. In OCT, an A-scan is a one-dimensional scan along the depth axis. A B-scan along another direction, together with A-scan, will generate a cross-section image where signal strength is translated to brightness. Although a few three dimension implementations of OCT have been reported [6], most of these methods deploy different schemes to achieve the secondary dimension scan (B-Scan), which will be combined with the intrinsic OCT depth scan (A-Scan) to form two-dimension images.

The most common application of endoscopic systems is to provide guidance and real-time monitoring during surgeries [11-12], for which a hand-held acquisition system is very much desired and often times inevitable. FIG. 1 illustrates a vitrectomy in ophthalmic surgery [13]. A vitrectomy is a surgical procedure to remove the vitreous humor (i.e., the clear gel that fills the space between the lens and retina of the eyeball) where surgeons insert an endoscopic needle 102 through a standard cannula 104 or scleral incisions (incisions into the sclera [also known as the white of the eye]) on the patient's eye to examine the remnant vitreous [14]. As illustrated, the endoscopic needle may illuminate 106 the organ or object under inspection, collect, and transmit back the reflected signal for image reconstruction.

Since image reconstruction always depends on the relative position between the object and the image acquirer (e.g., the needle 102, in the vitrectomy application), the time-varying position of the image acquirer, like shaking or vibration, imposes a significant impact on the acquired image. While different schemes have different gain, almost all of them have the intrinsic difficulty in this scenario to resolve the real image from the distortion and skew by the shaking and vibration of the image acquirer, which are usually from the operator's hand.

SUMMARY OF THE INVENTION

One or more embodiments of the invention utilize a position and motion tracking system and method to eliminate the distortion and skew due to the shaking and vibration in hand-held endoscopic applications. Embodiments may further provides means to reconstruct images according to the relative position between the object and the image acquirer.

BRIEF DESCRIPTION OF THE DRAWINGS

Referring now to the drawings in which like reference numbers represent corresponding parts throughout.

DETAILED DESCRIPTION OF THE PREFERRED EMBODIMENTS

In the following description, reference is made to the accompanying drawings which form a part hereof, and which is shown, by way of illustration, several embodiments of the present invention. It is understood that other embodiments may be utilized and structural changes may be made without departing from the scope of the present invention.

Overview

The basic idea of one or more embodiments of the invention is to track and record the relative position change between the image acquirer and the object being examined and use relative position change to calibrate and correct the acquired image that is displayed to the user (e.g., for use during surgery).

Structural Overview

Figure 1:
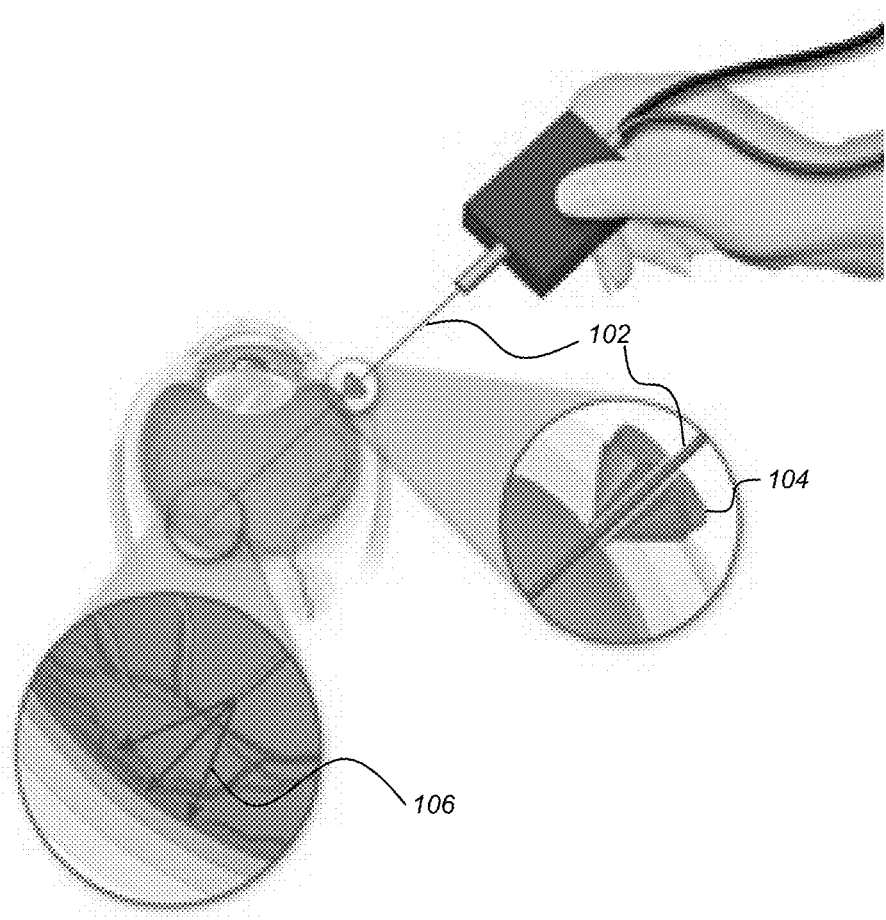
FIG. 1 illustrates a vitrectomy in ophthalmic surgery.
Figure 2:
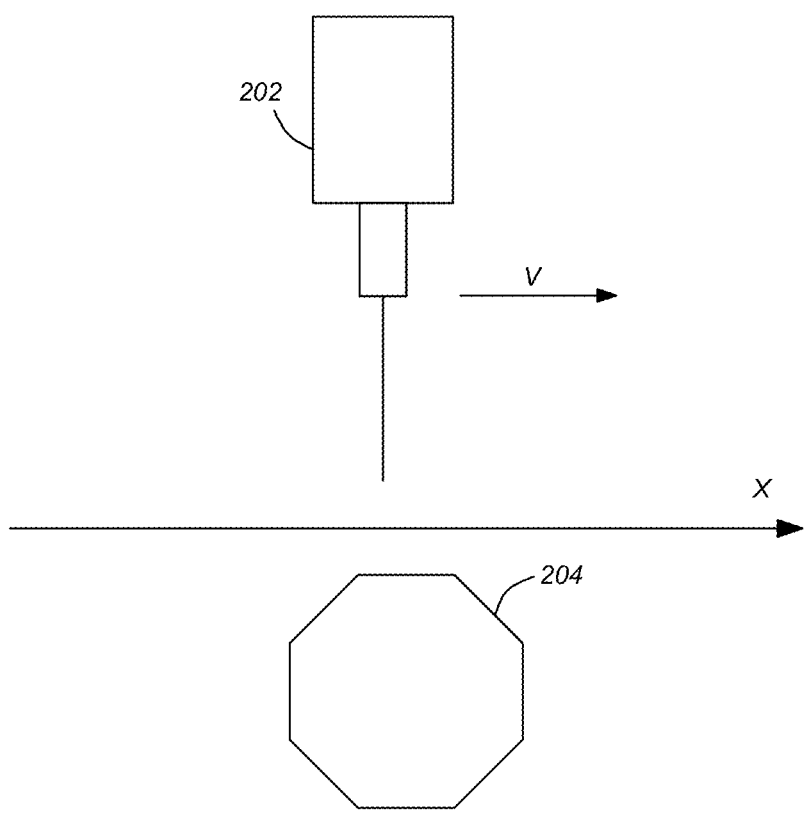
FIG. 2 illustrates a basic image acquiring structure and object to be imaged in accordance with one or more embodiments of the invention.

FIG. 2 illustrates a basic image acquiring structure and object to be imaged in accordance with one or more embodiments of the invention. As illustrated, a image acquirer 202 (e.g., an endoscopic needle or other sensing probe) is moving (V) along a single dimension (X) (i.e. on the X-axis) in order to image object 204.

Figure 3:
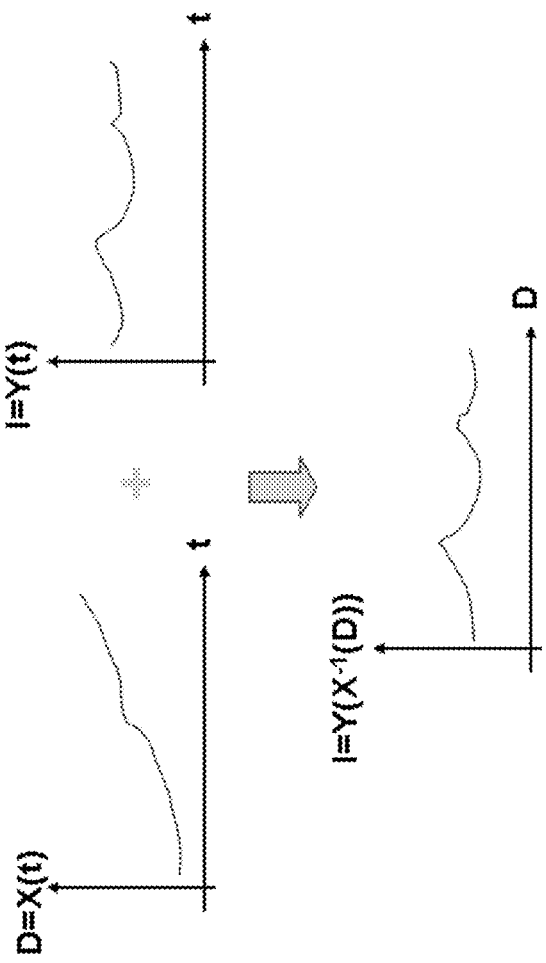
FIGS. 3A-3C illustrate the principle of image reconstruction in a one-dimensional case (e.g., based on FIG. 2) in accordance with one or more embodiments of the invention.

FIGS. 3A-3C illustrate the principle of image reconstruction in a one-dimensional case (e.g., based on FIG. 2) in accordance with one or more embodiments of the invention. FIG. 3A illustrates the image acquirer's movement V which can be characterized by the displacement function D=X(t) (as a function of time). In general, movement V does not have a constant velocity and X(t) might have a rather complicated form because of the shaking and vibration of human hands.

FIG. 3B illustrates local image information (of the object 204) acquired by image acquirer 202. The local image information is also a function of time, which can be represented by a scalar I=Y(t). While the image acquirer 202 keeps acquiring local image information from the object 204, a tracking system is also utilized to obtain the displacement information X(t) and record it. Upon receiving these two set of information (i.e., the image acquirer's movement V [D=X(t)] and local image information [I=Y(t)]), a reconstruction can be easily completed through the following series of steps:

(1) Compute the inverse function of D=X(t) as t=$X^{-1}$(D);
(2) Substitute t=$X^{-1}$(D) into I=Y(t); and
(3) Obtain the relationship between displacement and local image information I=Y($X^{-1}$(D)), which provides the local image information profile along the scanning direction. FIG. 3C illustrates such a profile in accordance with one or more embodiments of the invention.

Once these steps have been completed, the detail form of the function X(t) (which represents the movement/displacement of the image acquirer 202) is canceled out. Thus, the distortion and skew introduced by shaking and vibration are also corrected while reconstructing the real images.

Hand-Held Endoscopic Applications

For hand-held endoscopic applications, the tracking (i.e., the measurement of the movement/displacement of the image acquirer 202) includes two stages: (1) Position Tracking; and (2) Motion Tracking. The Position Tracking provides the first-level position information by sampling and recording the trace of the acquirer 202 or the trace of an agency which has a deterministic relationship with that of the acquirer. In some fast and non-uniform scanning applications, such as [6] [10], the sampled displacement data from the first stage might not be dense enough to reconstruct the image. Therefore, a second stage, Motion Tracking may be used to interpolate the displacement data by applying knowledge of the dynamics of the acquirer 202, such as acceleration.

Position Tracking

Figure 4:
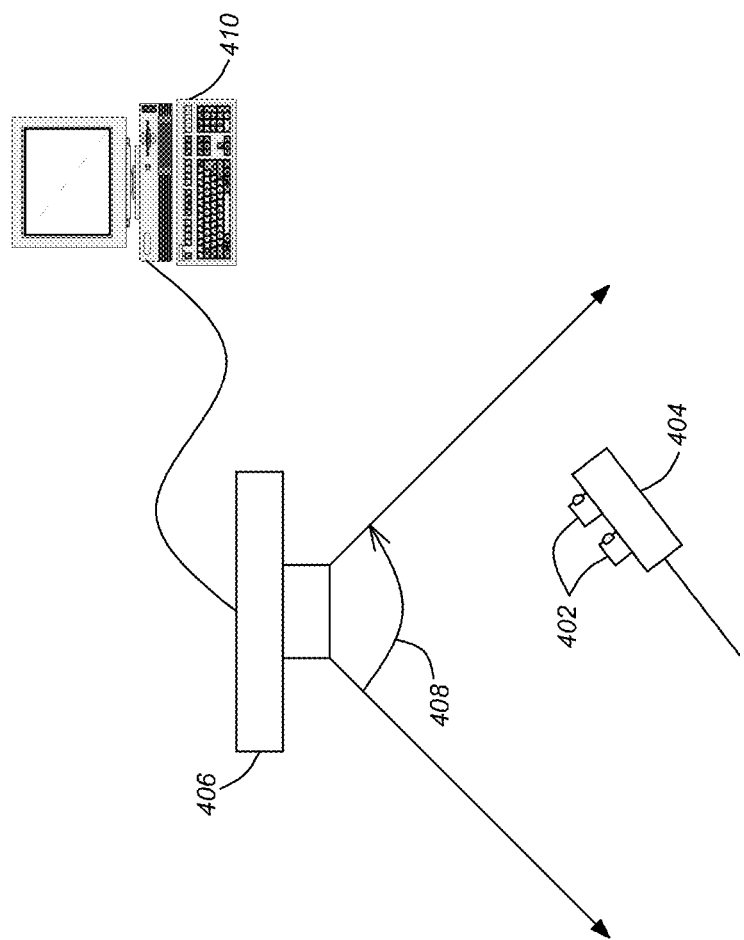
FIG. 4 illustrates a laser/LED beam assisted Position Tracking system used in accordance with one or more embodiments of the invention.

One or more embodiments of the invention may provide for position tracking using a laser or LED (light-emitting diode). FIG. 4 illustrates a laser/LED beam assisted Position Tracking system used in accordance with one or more embodiments of the invention.

In the illustrated configuration, two light sources 402 (e.g., laser diodes/LEDs), as agents of the image acquirer, are attached to the hand-held device 404. An image sensor 406 (having field of view 408) and data acquisition system 410 are used to gain displacement information of the device 404 through the emitted light from agents (i.e., from light sources 402).

The initial geometry condition can be used to perform a spatial calibration. More information, such as the orientation and rotation of the device 404, can be obtained with multiple light sources 402 and a more sophisticated multi-point tracking algorithm. The displacement information mentioned in this documents might usually include both the translation and rotation of the device.

The field of view 408 of the image sensor 406 may define the working range of the system. With the same field of view 408 (the angle), the further the device 404 is apart from the image sensor 406, the larger the working range will be. However, as the working range increases, the tracking resolution is reduced, which is usually a tradeoff during system design. A careful selection of such parameters (e.g., distance between device 404 and image sensor 406, field of view angle 408, etc.) may be used to optimize the system in both cost and performance.

An alternative implementation may include the placement of the image sensor 406 on the hand-held device 404 but the light sources 402 off-site. Such an implementation has the same operation principle and techniques can be shared among similar schemes.

Data Acquisition System Embodiments

Data acquisition system 410 may consist of a computer including a processor and memory. Thus, embodiments of the invention are typically implemented using a computer data acquisition system 410, which generally includes, a display device, data storage devices, cursor control devices, and other devices. Those skilled in the art will recognize that any combination of the above components, or any number of different components, peripherals, and other devices, may be used with the computer data acquisition system 410. In one or more embodiments, instructions are implemented within the computer data acquisition system 410 and are tangibly embodied in a computer-readable medium, e.g., a data storage device, which could include one or more fixed or removable data storage devices, such as a zip drive, floppy disc drive, hard drive, CD-ROM drive, DVD drive, tape drive, etc.

Further, instructions may be comprised of instructions which, when read and executed by the computer data acquisition system 410, causes the computer data acquisition system 410 to perform the steps necessary to implement and/or use the present invention. Instructions and/or operating instructions may also be tangibly embodied in a memory and/or data communications devices of the computer data acquisition system 410, thereby making a computer program product or article of manufacture according to the invention. As such, the terms "article of manufacture" and "computer program product" as used herein are intended to encompass a computer program accessible from any computer readable device or media. In addition, a computer readable storage medium may be encoded with computer program instructions which when accessed by a computer cause the computer to load the program instructions to a memory therein creating a special purpose data structure causing the computer to operate as a specially programmed computer that executes a method for image reconstruction.

Those skilled in the art will recognize that the exemplary environment illustrated in FIG. 4 is not intended to limit the present invention. Indeed, those skilled in the art will recognize that other alternative environments may be used without departing from the scope of the present invention.

Motion Tracking by a Motion Sensor

In the case of fast scanning, a motion sensor may be attached to the hand-held device 404 to sense the detail parameters of its motion. Many motion sensors are commercially available right now, such as ADXL330™ small low power 3-axis accelerometer manufactured by Analog Devices™. Depending on the sensor selected, different signal types (voltage or current) and formats (digital or analog) may be provided.

Figure 5:
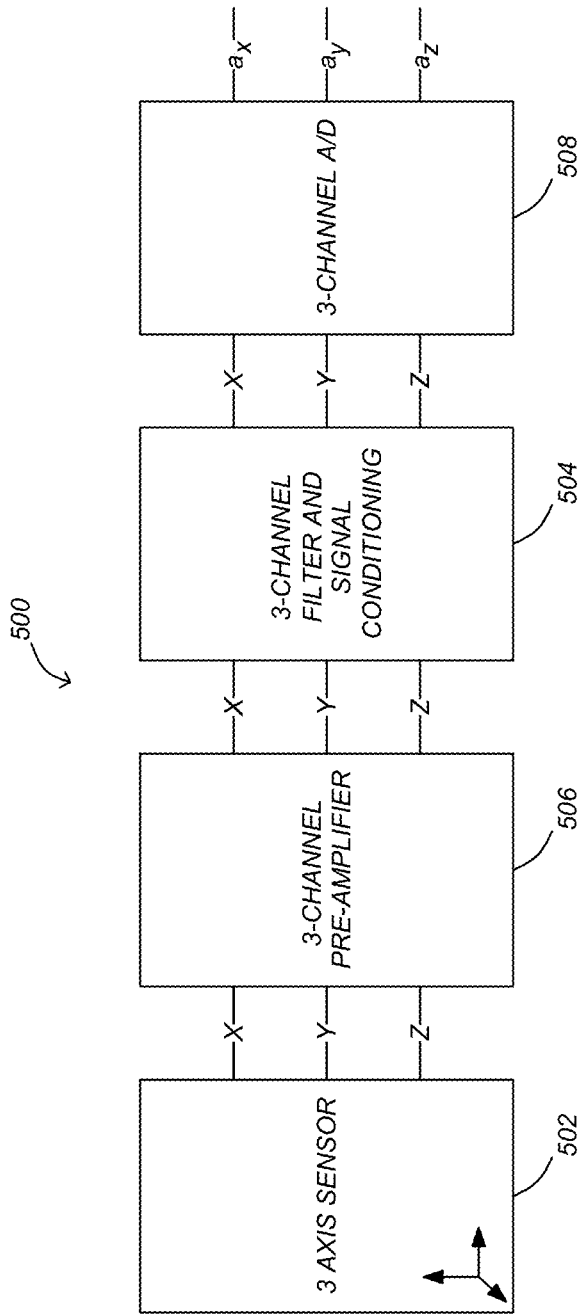
FIG. 5 illustrates a functional block diagram of a typical motion sensor in accordance with one or more embodiments of the invention.

FIG. 5 illustrates a functional block diagram of a typical motion sensor 500 in accordance with one or more embodiments of the invention. A 3-axis micromachined accelerometer 502 and signal conditioning circuitry 504 provide an open-loop acceleration measurement architecture. The acceleration signals (X,Y,Z) from the 3 axis sensor 502 are first amplified via a 3-channel pre-amplifier 506, filtered thereafter (e.g., via a 3-channel filter and signal conditional circuit 504), and then digitized (e.g., using a 3-channel analog to digital convertor 508).

The output from the sensor 500 consists of digital signals $(a_x, a_y, a_z)$ with enough accuracy representing the acceleration along all three axis (X,Y,Z). Based on the motion information of the device given by the motion sensor 500, interpolation can be made to achieve more spatial samples besides the samples acquired on the above-described stage of Position Tracking Depending on the accuracy requirement, different sensors 500 can be used to maximize the performance and minimize the complexity and cost.

Central Control System

Figure 6:
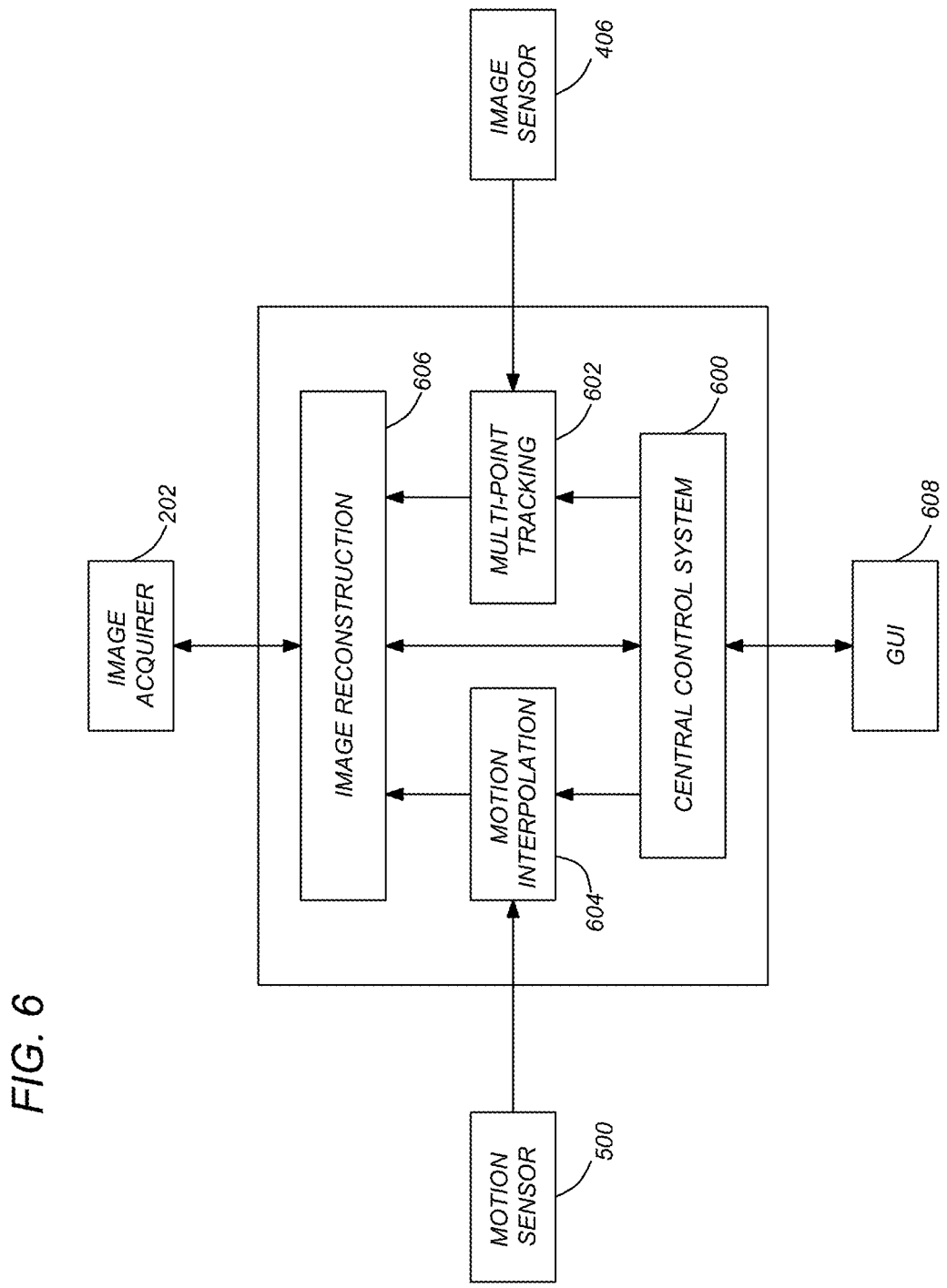
FIG. 6 illustrates a central control system used to synchronize all of the different components of the image reconstruction system in accordance with one or more embodiments of the invention.

The above two stages (position tracking and motion tracking) are synchronized by a central control system so that the interpolation can be made in the correct time order. FIG. 6 illustrates a central control system 600 used to synchronize all of the different components of the image reconstruction system in accordance with one or more embodiments of the invention.

To reconstruct the image, the central control system 600 not only synchronizes the position tracking and motion tracking, but the control system 600 also synchronizes the image acquisition 202. To synchronize all of the components, the central control system 600 manages the motion interpolation 604 of motion tracking (i.e., the motion sensor 500), the mutli-point tracking algorithm 602 of position tracking (i.e., from the image sensor 406) and the computation for image reconstruction 606.

The information from the two tracking stages can be organized and very well utilized while reconstructing images from the data out of the acquisition system 202. Typically the control system 600 will communicate with users through a GUI (graphical user interface 608 [e.g., on a computer 410]) to obtain system settings and output the reconstructed images to users.

As described above, the overall system may be PC-based (or based on any type of a computer) but can also be implemented into an embedded system. Depending on the frame rate and the amount of data to be processed, realtime implementation may also be provided.

In view of the above, it can be seen that the central control system 600 communicates with the motion interpolation component 604, the multi-point tracking component 602, and the image reconstruction component 606 to provide output to the GUI 608. In this regard, the central control system 600 transforms data from the image acquirer (e.g., via the endoscopic needle) into a visually depictable form in the GUI 608. As illustrated, the image reconstruction 606 also receives data from the motion interpolation component 604, the multi-point tracking component 602 and communicates with the central control system 600 and image acquirer 202.

Logical Flow

Figure 7:
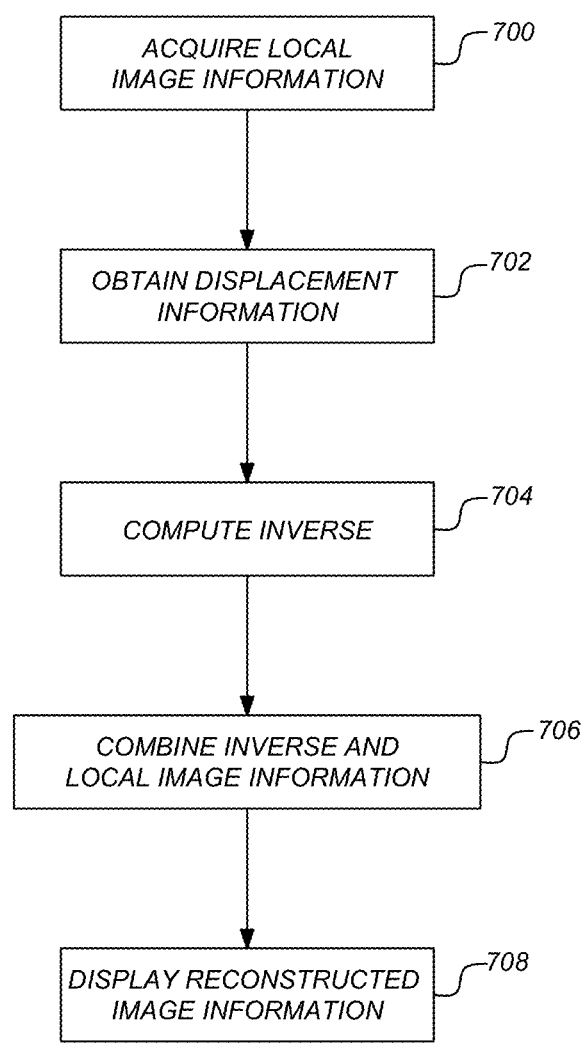
FIG. 7 illustrates the logical flow for reconstructing an image in accordance with one or more embodiments of the invention.

FIG. 7 illustrates the logical flow for reconstructing an image in accordance with one or more embodiments of the invention.

At step 700, a hand-held image acquisition device acquires local image information from a physical object. Such a hand-held image acquisition device may be an optical coherence tomography (OCT) based device such as an OCT based needle endoscope. Alternatively, the hand-held image acquisition device may be any type of sensing probe such as an ultrasound imaging probe.

At step 702 (which may be performed simultaneously with step 700), a tracking system obtains displacement information for the hand-held acquisition device while the device is acquiring the local image information. As described above, the tracking system may be a position tracking component configured to provide position information by sampling and recording a trace of the hand-held image acquisition device.

Further, an example of the position tracking component may be a laser/LED beam or other light sources acting as agents of the device assisted position tracking system. In such an embodiment, the sampling and recording are performed by tracing a movement of the device through light emitted from the agents on it. Alternatively, the position tracking may be conducted via ultrasound. Such displacement and position information may consist of both the translation and rotation of the hand-held acquisition device (e.g., more than a one-dimensional translation operation).

In addition, the tracking system may include a motion tracking component that is configured to interpolate the displacement information based on a knowledge of the dynamics of the hand-held device, such as acceleration. In this regard, an accelerometer may provide acceleration signals, an amplifier may amplify the acceleration signals, a filter and signal conditioning component may filter the amplified acceleration signals, and an analog/digital converter may digitize the filtered amplified acceleration signals. Further, additional parameters (i.e., of the hand-held acquisition device) may also be tracked.

Steps 704 and 706 may be performed by an image reconstruction system. At step 704, the inverse of the displacement information is computed. At step 706, the inverse is combined with the local image information to transform the local image information into a reconstructed local image information profile. Such steps may further include a central control system that synchronizes and manages the local image information, the displacement information, and the computation and transformation for image reconstruction.

Lastly, at step 708, a display device is configured to display the reconstructed local image information profile.

Thus, the object is transformed (via signals from the hand-held image acquisition device) into a reconstructed image without image distortion and skew caused by the shaking and vibration of human hands (which is then displayed to the user).

CONCLUSION

This concludes the description of the preferred embodiment of the invention. The following describes some alternative embodiments for accomplishing the present invention. For example, any type of computer, such as a mainframe, minicomputer, or personal computer, or computer configuration, such as a timesharing mainframe, local area network, or standalone personal computer, could be used with the present invention. In summary, embodiments of the invention provide the ability to reconstruct an image using position and motion tracking to eliminate the distortion and skew due to shaking and vibration in hand-held image acquiring mechanisms.

Embodiments of the invention are not limited to the OCT-based systems. Since embodiments of the invention track the motion and position of a hand-held device, the concepts described herein can be applied to any type of hand-held imaging acquisition system, regardless of their operation principle and detail realizations, such as [3-10]. Moreover, embodiments of the invention can be implanted into many current OCT endoscopic devices and used to correct the image distortion and skew caused by shaking and vibration of human hands thereby enhancing the overall system performance.

Another embodiment of the invention includes a simple, low cost, non-scanning OCT probe, which does not have B-scan capability intrinsically. In such an embodiment, the probe may be manually scanned over the object while tracking its displacement information. Thus this information can be used to reconstruct image and enable a very flexible manual-fashion B-scan.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

REFERENCES

[1] D. Huang, E. A. Swanson, C. P. Lin, J. S. Schuman, W. G. Stinson, W. Chang, M. R. Hee, T. Flotte, K. Gregory, C. A. Puliafito, J. G. Fujimoto, "Optical coherence tomography," Science 254, 1178-1181 (1991).
[2] Schmitt, J. M., S. L. Lee, and K. M. Yung, "An optical coherence microscope with enhanced resolving power in thick tissue," Optics Communications 142(4-6), 203-207 (1997).
[3] G. J. Tearney, S. A. Boppart, B. E. Bouma, M. E. Brezinski, N. J. Weissman, J. F. Southern, and J. G. Fujimoto, "Scanning single-mode fiber optic catheter-endoscope for optical coherence tomography," Opt. Lett. 21, 543-545 (1996).
[4] X. Li, C. Chudoba, T. Ko, C. Pitris, and J. G. Fujimoto, "Imaging needle for optical coherence tomography," Opt. Lett. 25, 1520-1522 (2000).
[5] P. R. Herz, Y. Chen, A. D. Aguirre, K. Schneider, P. Hsiung, J. G. Fujimoto, K. Madden, J. Schmitt, J. Goodnow, and C. Petersen, "Micromotor endoscope catheter for in vivo, ultrahigh-resolution optical coherence tomography," Opt. Lett. 29, 2261-2263 (2004).
[6] J. Su, J. Zhang, L. Yu, and Z. Chen, "In vivo three-dimensional microelectromechanical endoscopic swept source optical coherence tomography," Opt. Express 15, 10390-10396 (2007).
[7] T. Xie, H. Xie, G. K. Fedder, and Y. Pan, "Endoscopic optical coherence tomography with a modified microelectromechanical systems mirror for detection of bladder cancers," Appl. Opt. 42, 6422-6426 (2003).
[8] X. Liu, M. J. Cobb, Y. Chen, M. B. Kimmey, and X. Li, "Rapid-scanning forward-imaging miniature endoscope for real-time optical coherence tomography," Opt. Lett. 29, 1763-1765 (2004).
[9] T. Xie, S. Guo, Z. Chen, D. Mukai, and M. Brenner, "GRIN lens rod based probe for endoscopic spectral domain optical coherence tomography with fast dynamic focus tracking," Opt. Express 14, 3238-3246 (2006).
[10] J. Wu, M. Conry, C. Gu, F. Wang, Z. Yaqoob, and C. Yang. "Paired-angle-rotation scanning optical coherence tomography forward-imaging probe," Opt. Lett., 31, 1265-1267 (2006).
[11] Kelling, G., "Endoscopy of the esophagus and stomach". Lancet, 1900. 1: p. 1189-1198.
[12] Killian, G., "On direct endoscopy of the upper air passages and esophagus: Its diagnostic and therapeutic value in the search for and removal of foreign bodies". British Medical Journal, 1902. 1902: p. 569-571.
[13] R. Machemer, "The development of pars plana vitrectomy: a personal account," Graefes Arch. Clin. Exp. Ophthalmol. 233, 453-68 (1995).
[14] B. Povazay, K. Bizheva, B. Hermann, A. Unterhuber, H. Sattmann, A. Fercher, W. Drexler, C. Schubert, P. Ahnelt, M. Mei, R. Holzwarth, W. Wadsworth, J. Knight, and P. S. J. Russell, "Enhanced visualization of choroidal vessels using ultrahigh resolution ophthalmic OCT at 1050 nm," Opt. Express 11, 1980-1986 (2003).

What is claimed is:

1. An apparatus for reconstructing an image comprising:
    (a) a hand-held image acquisition device configured to acquire local image information from a physical object, wherein the local image information is a function of time;
    (b) a tracking system comprising:
        (i) an image sensor that is apart from the hand-held image acquisition device;
        (ii) the image sensor is configured to obtain displacement information for the hand-held acquisition device while the hand-held acquisition device is acquiring the local image information; and
        (iii) the displacement information is represented by a displacement function as a function of time;
    (c) an image reconstruction system configured to:
        (i) compute an inverse of the displacement function;
        (ii) combine, based on time, the inverse of the displacement function with the local image information to transform the local image information into a reconstructed local image information profile; and
    (d) a display device configured to display the reconstructed local image information profile.

2. The apparatus of claim 1, wherein the hand-held image acquisition device comprises an optical coherence tomography (OCT) based device.

3. The apparatus of claim 1, wherein the hand-held image acquisition device comprises an ultrasound imaging probe.

4. The apparatus of claim 2, wherein the hand-held image acquisition device comprises an OCT based needle endoscope.

5. The apparatus of claim 1, wherein the tracking system comprises a position tracking component configured to provide position information by sampling and recording a trace of the hand-held image acquisition device.

6. The apparatus of claim 5, wherein:
    the position tracking component comprises a laser/LED beam assisted position tracking system; and
    the position information is recorded and sampled by tracing a movement of the hand-held image acquisition device through light emitted from the laser/LED beam assisted position tracking system.

7. The apparatus of claim 1, wherein the image reconstruction system further comprises a central control system configured to synchronize and manage:
- the local image information acquired from the hand-held image acquisition device;
- the displacement information obtained by the tracking system; and
- the computation and the transformation for image reconstruction.

8. A method for reconstructing an image for an object, comprising:
- (a) acquiring, using a hand-held image acquisition device, local image information from a physical object, wherein the local image information is a function of time;
- (b) obtaining displacement information for the hand-held acquisition device while the hand-held acquisition device is acquiring the local image information, wherein:
  - (i) the displacement information is obtained by an image sensor that is apart from the hand-held image acquisition device; and
  - (ii) the displacement information is represented by a displacement function as a function of time;
- (c) computing an inverse of the displacement function;
- (d) combining, based on time, the inverse of the displacement function with the local image information to transform the local image information into a reconstructed local image information profile; and
- (e) displaying the reconstructed local image information profile.

9. The method of claim 8, wherein the hand-held image acquisition device comprises an optical coherence tomography (OCT) based device.

10. The method of claim 8, wherein the hand-held image acquisition device comprises an ultrasound imaging probe.

11. The method of claim 9, wherein the hand-held image acquisition device comprises an OCT based needle endoscope.

12. The method of claim 8, wherein displacement information is obtained by sampling and recording a trace of the hand-held image acquisition device.

13. The method of claim 12, wherein the recording and sampling is provided:
- using a laser/LED beam assisted position tracking system; and
- by tracing a movement of the hand-held image acquisition device through light emitted from the laser/LED beam assisted position tracking system.

14. The method of claim 8, further comprising synchronizing and managing:
- the local image information;
- the displacement information; and
- the computation and the transformation for image reconstruction.

15. The apparatus of claim 1, wherein:
- a field of view of the image sensor defines a working range of the tracking system; and
- the tracking system is optically based.

16. The apparatus of claim 1, wherein the displacement information obtained by the image sensor comprises rotation information and translation information of the hand-held image acquisition device.

17. The method of claim 8, wherein:
- a field of view of the image sensor defines a working range for obtaining the displacement information; and
- the image sensor is optically based.

18. The method of claim 8, wherein the displacement information obtained by the image sensor comprises rotation information and translation information of the hand-held image acquisition device.

19. The apparatus of claim 1, wherein the local image information comprises a scalar representation as a function of time.

20. The method of claim 8, wherein the local image information comprises a scalar representation as a function of time.

* * * * *